(12) United States Patent
Baek et al.

(10) Patent No.: US 12,311,024 B2
(45) Date of Patent: May 27, 2025

(54) CANCER CELL-TARGETED DRUG DELIVERY CARRIER AND COMPOSITION FOR PROMOTING PHOTO-THERMAL TREATMENT EFFECTS, BOTH OF WHICH CONTAIN M1 MACROPHAGES AS ACTIVE INGREDIENT

(71) Applicant: KOREA UNIVERSITY RESEARCH AND BUSINESS FOUNDATION, Seoul (KR)

(72) Inventors: Seung Kuk Baek, Seoul (KR); Nu Ri Im, Seoul (KR)

(73) Assignee: KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 742 days.

(21) Appl. No.: 17/626,043

(22) PCT Filed: Jul. 13, 2020

(86) PCT No.: PCT/KR2020/009173
§ 371 (c)(1),
(2) Date: Jan. 10, 2022

(87) PCT Pub. No.: WO2021/010698
PCT Pub. Date: Jan. 21, 2021

(65) Prior Publication Data
US 2022/0249666 A1    Aug. 11, 2022

(30) Foreign Application Priority Data
Jul. 12, 2019 (KR) .................. 10-2019-0084665

(51) Int. Cl.
| | | |
|---|---|---|
| *A61K 41/00* | (2020.01) | |
| *A61K 31/337* | (2006.01) | |
| *A61K 31/44* | (2006.01) | |
| *A61K 31/475* | (2006.01) | |
| *A61K 31/519* | (2006.01) | |
| *A61K 31/675* | (2006.01) | |
| *A61K 31/704* | (2006.01) | |
| *A61K 31/7048* | (2006.01) | |
| *A61K 31/7068* | (2006.01) | |
| *A61K 33/242* | (2019.01) | |
| *A61K 33/243* | (2019.01) | |
| *A61K 40/17* | (2025.01) | |
| *A61K 40/24* | (2025.01) | |
| *A61K 40/42* | (2025.01) | |
| *A61K 47/69* | (2017.01) | |
| *A61P 35/00* | (2006.01) | |
| *C12N 5/0786* | (2010.01) | |

(52) U.S. Cl.
CPC ........ *A61K 41/0028* (2013.01); *A61K 31/337* (2013.01); *A61K 31/44* (2013.01); *A61K 31/475* (2013.01); *A61K 31/519* (2013.01); *A61K 31/675* (2013.01); *A61K 31/704* (2013.01); *A61K 31/7048* (2013.01); *A61K 31/7068* (2013.01); *A61K 33/242* (2019.01); *A61K 33/243* (2019.01); *A61K 40/17* (2025.01); *A61K 40/24* (2025.01); *A61K 40/42* (2025.01); *A61K 47/6923* (2017.08); *A61P 35/00* (2018.01); *C12N 5/0645* (2013.01); *A61K 2239/31* (2023.05)

(58) Field of Classification Search
CPC .. A61K 41/0028; A61K 31/337; A61K 31/44; A61K 31/475; A61K 31/519; A61K 31/675; A61K 31/704; A61K 31/7048; A61K 31/7068; A61K 33/242; A61K 33/243; A61K 35/15; A61K 47/6923; A61K 38/12; A61K 39/4614; A61K 39/4622; A61K 39/4644; A61K 9/501; A61K 9/5063; A61K 2239/31; A61K 41/0052; A61K 45/06; A61K 47/02; A61K 47/44; A61P 35/00; C12N 2503/02; C12N 2529/10; C12N 2539/10; C12N 5/0645; C12N 2500/30; C12N 2501/24; C12N 2506/115
See application file for complete search history.

(56) References Cited

FOREIGN PATENT DOCUMENTS

| | | |
|---|---|---|
| CN | 106421810 A | 2/2017 |
| KR | 10-2018-0094883 A | 8/2018 |

OTHER PUBLICATIONS

Genin et al. (M1 and M2 macrophages derived from THP-1 cells differentially modulate the response of cancer cells to etoposide, BMC Cancer, 2015). (Year: 2015).*
Madsen et al. (Macrophages as Cell-Based Delivery Systems for Nanoshells in Photothermal Therapy, Annals of Biomedical Engineering, 2012 (Year: 2012).*
Pang et al. (Primary M1 macrophages as multifunctional carrier combined with PLGA nanoparticle delivering anticancer drug for efficient glioma therapy, Drug Delivery, 2018 (Year: 2018)*
(Continued)

*Primary Examiner* — Robert A Wax
*Assistant Examiner* — John Seungjai Kwon
(74) *Attorney, Agent, or Firm* — Casimir Jones, S.C.; Robert A. Goetz

(57) ABSTRACT

The present invention relates to a cancer cell-targeted drug delivery carrier, a composition for promoting photo-thermal treatment effects, and the like, which contain M1 macrophages as an active ingredient. The drug delivery carrier of the present invention uses the M1 macrophages mobility to tumor cells and the M1 macrophage penetrability into tumors, and can deliver drugs specifically to tumor and cancer tissues only, and, when performing photo-thermal treatment by loading M1 macrophages with a photosensitive material, can significantly increase the effects, and thus is expected to be effectively used for promoting cancer treatment effects.

2 Claims, 8 Drawing Sheets

(56) References Cited

OTHER PUBLICATIONS

Madsen et al. Macrophages as cell-based delivery systems for nanoshells in photothermal therapy. Ann Biomed Eng. Feb. 2012;40(2):507-15.
Pang et al. Primary M1 macrophages as multifunctional carrier combined with PLGA nanoparticle delivering anticancer drug for efficient glioma therapy. Drug Deliv. Nov. 2018;25(1):1922-1931.
International Search Report International Patent Application No. PCT/KR2020/009173, mailed Nov. 6, 2020, 4 pages.
Madsen, S.J. et al. Macrophages as Cell-Based Delivery Systems for Nanoshells in Photothermal Therapy. Annals of Biomedical Engineering. Feb. 2012, vol. 40, No. 2, pp. 507-515.
Pang, L. et al. Primary M1 macrophages as multifunctional carrier combined with PLGA nanoparticle delivering anticancer drug for efficient glioma therapy. Drug Delivery. 2018, No. 25, No. 1, pp. 1922-1931.
Genin, M. et al. M1 and M2 macrophages derived from THP-1 cells differentially modulate the response of cancer cells to etoposide. BMC Cancer. 2015, vol. 15, document 577, pp. 1-14.
Son, Joeun. Tumor-Associated Macrophages: From Mechanisms to Therapy. BRIC View. Mar. 15, 2016, document 2016-R06, pp. 1-11.
Dandekar, R. C. et al. Role of macrophages in malignancy, Ann Maxillofac Surg. Jul.-Dec. 2011; 1(2): 150-0154.
MacParland Sonya A. et al: "Phenotype Determindes Nanoparticle Uptake by Human Macrophages from Liver and Blood", ACS Nano, vol. 11, No. 3, Jan. 17, 2017 (Jan. 17, 2017), pp. 2428-2443, XP093078416, US.
Steen J. Madsen et al: "Nanoparticle-loaded macrophage-mediated photothermal therapy: potential for glioma treatment", Lasers in Medical Science, vol. 30, No. 4, Mar. 21, 2015 (Mar. 21, 2015), pp. 1357-1365, XP055333432, London.
Marie Genin et al: "M1 and M2 macrophages derived from THP-1 cells differentially modulate the response of cancer cells to etoposide", BMC Cancer, Biomed Central, London, GB, vol. 15, No. 1, Aug. 8, 2015 (Aug. 8, 2015), p. 577.
Huang Yen-Jang et al: "Modulation of Macrophage Phenotype by Biodegradable Polyurethane Nanoparticles: Possible Relation between Macrophage Polarization and Immune Response of Nanoparticles", Applied Materials & Interfaces, vol. 10, No. 23, May 18, 2018 (May 18, 2018), pp. 19436-19448.
Tang Hongbo et al: "Effect of monocytes/macrophages on the osteogenic differentiation of adipose-derived mesenchymal stromal cells in 3D co-culture spheroids", Tissue and Cell, vol. 49, No. 4, pp. 461-469.
Agata Mlynska et al: "Platinum sensitivity of ovarian cancer cells does not influence their ability to induce M2-type macrophage polarization", American Journal of Reproductive Immunology, Wiley-Blackwell Publishing, Inc, US, vol. 80, No. 3, Jun. 14, 2018 (Jun. 14, 2018), 11 pages.
S Kim I et al: "Effects of triethylene glycol dimethacrylate and hydroxyethyl methacrylate on macrophage polarization", International Endodontic Journal, Ackwell Scientific Publications, Oxford, BL, vol. 52, No. 7, Feb. 20, 2019 (Feb. 20, 2019), pp. 987-998.
Schoenenberger Angelina D et al: "Substrate fiber alignment mediates tendon cell response to inflammatory signaling", Acta Biomaterialia, Elsevier, Amsterdam, NL, vol. 71, Mar. 10, 2018 (Mar. 10, 2018), pp. 306-317.
Zhi-Chao Wang et al: "Deficiency in interleukin-10 production by M2 macrophages in eosinophilic chronic rhinosinusitis with nasal polyps", International Forum of Allergy & Rhinology, Wiley-Blackwell, Oxford, vol. 8, No. 11, Oct. 3, 2018 (Oct. 3, 2018), pp. 1323-1333.
Yang Shujun et al: "MicroRNA-2016a promotes M1 macrophages polarization and atherosclerosis progression by activating telomeraseviathe Smad3/NF-[kappa]B pathway", Biochimica Et Biophysica Acta. Molecular Basis of Disease, Amsterdam, NL, vol. 1865, No. 7, Jun. 27, 2018 (Jun. 27, 2018), pp. 1772-1781.
Julio M Rios De La Rosa et al: "The CD44-Mediated Uptake of Hyaluronic Acid-Based Carriers in Macrophages", Advanced Healthcare Materials, Wiley—V C H Verlag GMBH & Co. KGAA, DE, vol. 6, No. 4, Dec. 19, 2016 (Dec. 19, 2016), 11 pages.
Supplementary EP Search Report, EP Patent Application No. 20840898. 9, 6 pages.

\* cited by examiner

CANCER CELL-TARGETED DRUG DELIVERY CARRIER AND COMPOSITION FOR PROMOTING PHOTO-THERMAL TREATMENT EFFECTS, BOTH OF WHICH CONTAIN M1 MACROPHAGES AS ACTIVE INGREDIENT

TECHNICAL FIELD

The following description relates to a cancer cell-targeting drug delivery system containing M1 macrophages as an active ingredient and/or a composition for enhancing a photo-thermal treatment effect containing M1 macrophages as an active ingredient.

BACKGROUND ART

Photo-thermal treatment of cancer is an effective new cancer treatment technology that has recently been spotlighted. There are three main types of existing cancer treatment methods: the first is to remove the cancer via surgery. This method may remove visible and palpable cancer but may not remove small cancers and may have a limitation in that it cannot prevent cancer metastasis. The second is chemical treatment using anticancer drugs. The third is radiation therapy, which removes cancer by irradiating radiation to a site where there is cancer. The radiation therapy has a great effect on cancer that cannot be removed by surgery and is being studied in various fields. Currently, these three methods are used alone or in combination with each other to treat cancer. As each of the methods continues to develop, related papers thereon are continuously published worldwide. However, the cancer is still fear-causing and the cure percentage thereof is 50%. In most cases, surgery requires general anesthesia, and the surgical scars remain in the body. Moreover, when the cancer has metastasized, surgery is not helpful.

There are about 40 types of anticancer drugs that are being used for patients. They act on cancer cells to inhibit proliferation thereof but have the disadvantage of acting on normal cells at the same time. Treatment with most anticancer drugs slows nail growth, causes hair loss, and damage to the mucous membrane, thereby causing not only a sore mouth, but also diarrhea and abdominal pain due to the breakdown of the gastrointestinal mucosa. Further, hematopoietic cells are damaged, resulting in a decrease in white blood cells, red blood cells and platelets.

Further, the radiation therapy has a detrimental effect on the human body as in the anticancer drugs, as radiation that reaches the cancer to achieve its purpose causes damage to normal cells due to the nature of the radiation going straight.

However, the photo-thermal treatment method may use the fact that cancer cells are weaker to heat compared to normal cells and thus may place a photo-responsive material at a local location where cancer cells are located, and then generate heat via stimulating externally to selectively kill only cancer cells. It may be expected that the existing side effects may be minimized because the pure heat-generation effect is used in the photo-thermal treatment method.

Gold nanoparticles, nano-porous silica, carbon nanotubes, or magnetic iron oxide are used as photo-responsive materials for this photo-thermal treatment method. This photo-thermal treatment method using the nanomaterial has fewer side effects and is effective, compared to the convention cancer treatments. However, the nanomaterial itself is toxic. When the nanomaterial is near normal cells, not cancer cells, photo-thermal energy is applied thereto, such that there is a side effect that may also kill the normal cells.

Accordingly, in order to effectively photo-thermal treatment of cancer in vivo, development of a photoreactive compound for photo-thermal treatment which is easily excreted in vivo and thus has low potential toxicity, and uses a drug delivery system such that accumulation efficiency thereof in target cancer tissue and cancer cell targeting efficiency thereof are high, and has high exothermic efficiency is required.

On the other hand, TAM (tumor associated macrophage) is known as a macrophages involved in the growth, proliferation, and metastasis of cancer cells in the tumor (cancer) microenvironment. Macrophages are concentrated around the tumor and penetrate into the tumor, and are differentiated into M1 macrophages and M2 macrophages by the tumor (cancer) microenvironment. M1 macrophages is called CLS macrophages (Crown like structure macrophage), and causes the death of cancer cells and reduces the proliferation of tumors. Unlike the M1 macrophage, M2 macrophage called resident macrophage is known to induce angiogenesis in the cancer microenvironment to cause cancer cell metastasis.

Although research on a drug delivery system using the chemotaxis of macrophages to tumor cells is in progress, no technology thereon has been developed yet to be implemented. Further, the technology for inducing differentiation of macrophages into M1 and M2 macrophages is still lacking.

DISCLOSURE OF THE INVENTION

Technical Goals

An aspect provides M1 macrophages as a drug delivery system. The drug delivery system of the present disclosure may function as a composition for enhancing a photo-thermal treatment effect or a cancer cell-targeting anticancer drug depending on a material loaded thereon.

Accordingly, a purpose of the present disclosure is to provide a composition for enhancing the photo-thermal treatment effect containing the M1 macrophages having the photo-responsive material loaded thereon as an active ingredient.

Further, another purpose of the present disclosure is to provide a cancer cell-targeting drug delivery system containing the M1 macrophages as an active ingredient.

However, the technical purpose to be achieved by the present disclosure is not limited to the above-mentioned purpose, and other purposes not mentioned will be clearly understood by those skilled in the art from the following description.

Technical Solutions

In order to solve the above purposes, the present disclosure provides a composition for enhancing the photo-thermal treatment effect, the composition containing M1 macrophages having a photo-responsive material loaded thereon as an active ingredient.

In an implementation of the present disclosure, the photo-responsive material may include one or more materials selected from the group consisting of metallic nanoparticles, nano porous silica, carbon nanotube, and magnetic iron oxide ($Fe_3O_4$).

In another implementation of the present disclosure, the metal nanoparticles include gold nanoparticles and silver nanoparticles, wherein the gold nanoparticles may include one or more particles selected from the group consisting of gold nanorods, gold nanoshells, and gold nanocages.

In still another implementation of the present disclosure, the gold nanoparticles may be poly(lactic-co-glycolic) acid (PLGA)-core gold nanoshells.

Further, the present disclosure provides a method for enhancing the photo-thermal treatment effect, the method including a step of administering the M1 macrophages having the photo-responsive material loaded thereon to a subject. The subject is not limited particularly as long as it is a mammal in need of cancer treatment, and preferably a cancer patient (human). Further, the administration may be intravenous administration or local administration, but is not limited thereto.

Further, the present disclosure provides a cancer-targeted drug delivery system containing M1 macrophages as an active ingredient.

In an implementation of the present disclosure, the M1 macrophages may have an anticancer drug loaded thereon. In the present disclosure, M1 macrophages having an anticancer drug loaded thereon may be provided as a pharmaceutical composition for preventing or treating cancer.

In another implementation of the present disclosure, the anticancer drug may be at least one selected from the group consisting of doxorubicin, pemetrexed, gemcitabine, paclitaxel, vincristine, daunorubicin, vinblastine, actinomycin-D, docetaxel, etoposide, teniposide, bisantrene, homoharringtonine, Gleevec (STI-571), cisplatin, 5-fluorouracil, methotrexate, busulfan, chlorambucil, cyclophosphamide, melphalan, nitrogen mustard, nitrosourea, cetuximab, and sorafenib.

In still another implementation of the present disclosure, the M1 macrophages may have the above-described photo-responsive material and the anticancer drug loaded thereon.

In still another implementation of the present disclosure, each of the anticancer drug and the photo-responsive material may be loaded at a concentration of 0.5 to 12.5 μg/ml, preferably 1 to 5 μg/ml, more preferably 2.5 μg/ml.

In still another implementation of the present disclosure, the metal nanoparticles may be PLGA-core gold nanoshells. The anticancer drug may be doxorubicin. Each of the PLGA-core gold nanoshells and the anticancer drug may be loaded at a concentration of 0.5 to 12.5 μg/ml, preferably 1 to 5 μg/ml, more preferably 2.5 μg/ml.

Further, the present disclosure provides a cancer treatment method including a step of administering an anticancer drug-loaded M1 macrophages to a subject and provides a method for enhancing the cancer treatment effect including a step of administering an anticancer drug-loaded M1 macrophages to a subject. The subject is not limited particularly as long as it is a mammal in need of cancer treatment, and preferably a cancer patient (human). Further, the administration may be intravenous administration or local administration, but is not limited thereto.

In an implementation of the present disclosure, the M1 macrophages may be administered to the subject 1 to 3 times a day, preferably once a day.

Further, the present disclosure provides use of an anticancer drug-loaded M1 macrophages for producing a cancer therapeutic drug.

Further, the present disclosure provides a method for inducing differentiation of undifferentiated macrophages into M1 macrophages, the method including following steps:

(1) treating undifferentiated macrophages with PMA (Phorbol-12 Myristate 13-Acetate) to induce an M0 macrophage state; and (2) treating the M0 macrophages with IFN-γ (Interferon gamma) to induce differentiation thereof into the M1 macrophages.

In an implementation of the present disclosure, the treatment with IFN-γ in the step (2) may be performed for 24 to 48 hours at a concentration of 100 to 400 μg/ml thereof, preferably for 24 hours at a concentration of 200 μg/ml thereof.

In another implementation of the present disclosure, the method may further include a step of resting the M0 macrophages for 3 to 9 days after the (1) step.

Advantageous Effects

The present disclosure suggests that the material loaded onto the M1 macrophages may be specifically delivered only to the tumor and cancer tissue based on the migration ability of the M1 macrophages into the tumor cells and the ability thereof to penetrate into the tumor. In particular, when the anticancer drug is loaded into the M1 macrophage, this has the effect of increasing its efficacy and reducing side effects thereof. In addition, when the photo-responsive material is loaded into the M1 macrophage, it is possible to enhance the photo-thermal treatment effect by reducing the movement time to cancer cells and increasing the penetration ability into the cancer cells. This may be a new treatment method that may treat residual cancer that cannot be treated with the existing treatment methods such as surgery, radiation, and anticancer drug treatment. The M1 macrophages may be provided as a drug delivery system and thus will be usefully used to enhance the therapeutic effect of cancer.

BEST MODE FOR CARRYING OUT THE INVENTION

Figure 1:
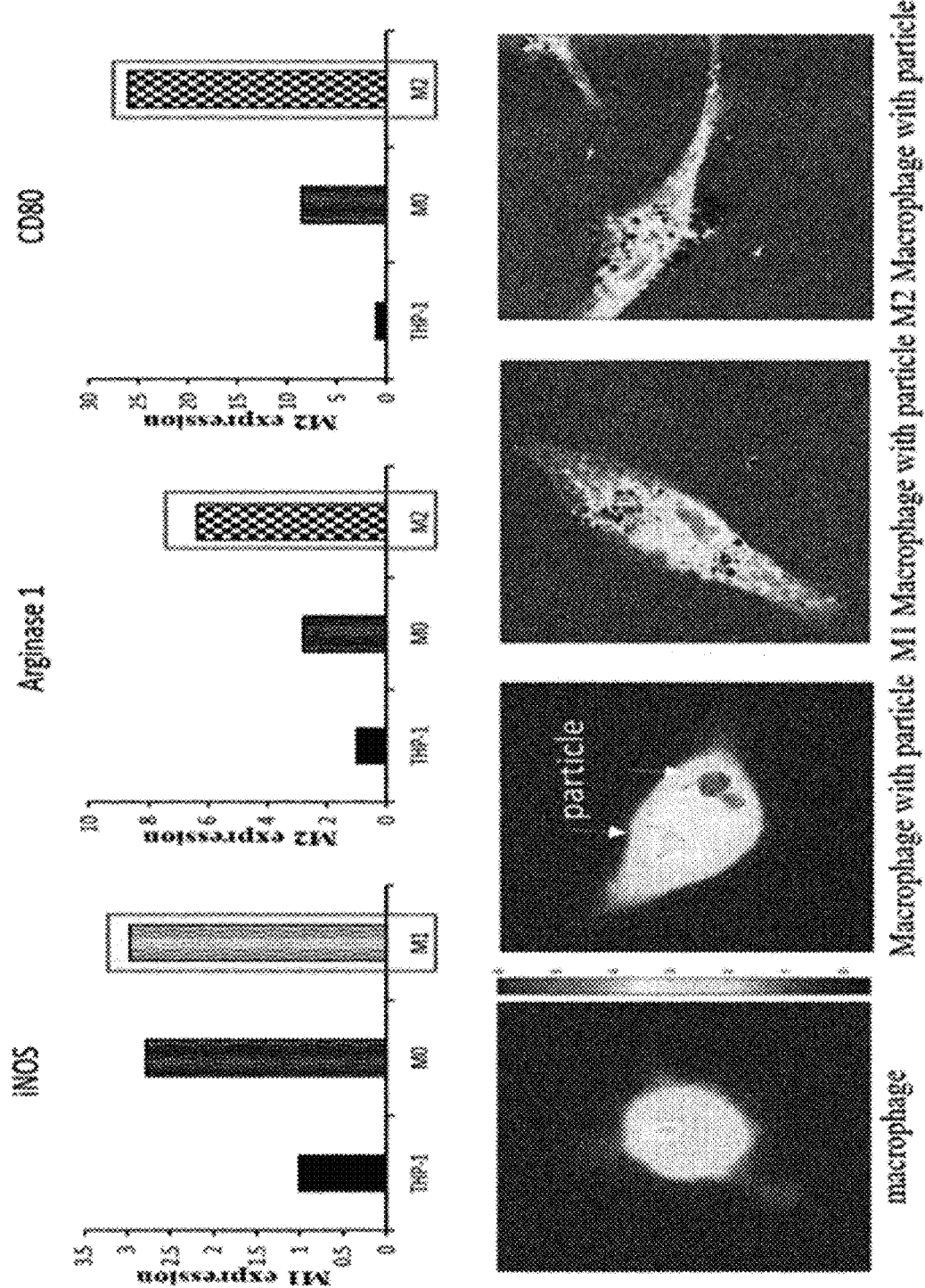
FIG. 1 is a diagram identifying of induced in vitro differentiation of macrophages into M1 or M2 macrophages.

The present inventors conducted follow-up studies based on the results of previous studies that identified that macrophages containing biodegradable nanoparticles (PLGA-core Gold Nanoshells) that absorb near-infrared wavelengths absorb near-infrared wavelengths. Based on the follow-up studies, we identified the chemotaxis of macrophages to tumors, and the invasion of macrophages into the tumors based on histological findings. Further, based on a result of testing the chemotaxis and penetration ability into tumor and/or cancer tissue according to the type of macrophage, it was identified that M1 macrophages has the fastest movement speed to the tumor and the best penetration into the tumor. Thus, we completed the present disclosure.

Macrophage is one of the phenotypes into which myeloid cells are finally differentiated. It is understood that myeloid cells mainly present in the bone marrow move into the tumor microenvironment through blood and differentiate into the macrophages. Recently, it has been known that the macrophages are dynamically polarized into M1-macrophages and M2-macrophages under various physiological and pathological conditions in vivo. M1-macrophages refer to a classically activated macrophage. The activation is made via stimuli such as external pathogens and interferon gamma. The M1-macrophages secrete IL-12 to induce an inflammatory response, and thus has a tumor suppressor effect in the tumor microenvironment. On the other hand, M2-macrophages are an alternatively activated (alternatively activated) macrophages. The activation is made via IL-4, IL-10, IL-13, and adrenocortical hormone. M2-macrophages are known to have anti-inflammatory action, and secrete IL-4, IL-10, and IL-13 to promote tumor growth.

In the present disclosure, M1 macrophages may form a cluster around the dead adipocytes, and are morphologically called CLS macrophages (Crown like structure Macrophage). The macrophages which have migrated to cancer tissues differentiate into M1 macrophages, which causes apoptosis of cancer cells and are identified based on the expression of iNOS.

According to one example of the present disclosure, undifferentiated macrophages were treated with PMA to induce an M0 state, and then M0 macrophages were treated with IFN-γ to allow the M0 macrophages to be differentiated into M1 macrophages (see Example 1).

According to another embodiment of the present disclosure, we transfected the luciferase gene into undifferentiated macrophages and M1 macrophages, which in turn were administered to immune-deficient mice injected with tumor cells. Then, luminescence was traced to identify the migration path of macrophages. Based on the luminescence tracing result, it was identified that the M1 macrophages had significantly faster migration speed to tumors than the undifferentiated macrophages had and had exceptionally superior penetrating power into the tumor. It was found that M1 macrophages were excellent for drug delivery to cancer and/or tumor (see Example 3).

On the other hand, in one embodiment of the present disclosure, we cultured M0, M1, and M2 macrophages having a photo-responsive material loaded thereon together with cancer cells, respectively, and irradiated a laser thereto. Then, the photo-thermal treatment effect was identified. Thus, it was identified that regardless of the concentration of macrophages treated on cancer cells, when photo-thermal treatment was performed by loading the photo-responsive material into the M1 macrophage, more cancer cells were killed, thereby remarkably increasing the photo-thermal treatment effect (See Example 4-1).

Further, in one embodiment of the present disclosure, PLGA-core gold nanoshells were loaded into the M1 macrophages which in turn were administered to immunodeficient mice injected with tumors. Thus, the photo-thermal treatment was performed thereon. Thus, it was identified that when using the M1 macrophages, the tumor removal effect was excellent compared to a case when using undifferentiated macrophages (see Example 4-2).

Accordingly, the present disclosure provides a composition for enhancing the photo-thermal treatment effect containing M1 macrophages having a photo-responsive material loaded thereon as an active ingredient, based on the ability of M1 macrophages to migrate to the tumor (cancer) and the penetration thereof into the tumor (cancer) tissue.

Photo-thermal treatment (PTT) uses the fact that the cancer cells are vulnerable to the heat, compared to normal cells, and thus places a photo-responsive material at a local location where cancer cells are located, and generates heat via external stimulation to selectively kill only cancer cells. This PTT uses the pure exothermic effect, so that the existing side effects may be minimized.

The photo-responsive material used for photo-thermal treatment is a material that responds to light and thus is activated. In anticancer treatment, the photo-responsive material may refer to a material that generates reactive oxygen species that may attack cancer cells in response to light.

In the present disclosure, non-limiting examples of the photo-responsive materials include metallic nanoparticles, nano porous silica, carbon nanotubes, magnetic iron oxide ($Fe_3O_4$), and the like.

Metal nanoparticles include gold nanoparticles and silver nanoparticles. Among them, gold nanoparticles have excellent light absorption, photothermal effect, biocompatibility, and stability against photobleaching. This satisfies the important requirements of photosensitizers: effective release of thermal energy, non-toxicity and stability in vivo. Gold nanoparticles being studied for photo-thermal treatment are anisotropic particles such as rod-shaped, cube-shaped, and core/shell structures designed to absorb light in the near-infrared region. In a specific embodiment of the present disclosure, gold nanoshells were used, and more specifically, a macrophage having a photo-responsive material loaded thereon was manufactured using the PLGA-core gold nanoshells.

On the other hand, anticancer drugs are generally drugs that target dividing/proliferating cells and induce apoptosis thereof and have cytotoxicity to normal cells. Accordingly, in one embodiment of the present disclosure, to identify the beneficial effect of M1 macrophages as an anticancer drug delivery system and whether the macrophages having an anticancer drug loaded thereon may induce cancer cell death while the macrophages are not killed before moving to cancer cells, we loaded various concentrations of PLGA and doxorubicin (DOX) into M1 macrophages and undifferentiated macrophages and then identified cell viability and cancer cell death over time. As a result, macrophages viability of 50% or more was observed at 2.5 μg/ml, which is the lowest concentration among the concentrations in which cancer cell death occurs for 72 hours after 12 hours required for the migration time of macrophages to cancer cells. Thus, we identified the usefulness of cancer cell targeting drug delivery of M1 macrophages having the PLGA and anticancer drug loaded thereon at the concentration of 2.5 μg/ml (see Example 5-2).

Accordingly, the present inventors provide a cancer cell-targeting drug delivery system containing M1 macrophages as an active ingredient.

The cancer cell-targeting drug delivery system according to the present disclosure may be an M1 macrophages containing an anticancer drug or a mixture of an anticancer drug and particles. The anticancer drug is not limited particularly as long as it inhibits the growth, proliferation and/or metastasis of cancer cells. Inhibition of cancer cell growth, proliferation, and/or metastasis may be achieved by a method of creating a tumor microenvironment that interferes with the growth, proliferation, and/or metastasis of cancer cells by blocking angiogenesis in addition to direct cell action. Non-limiting examples of anticancer drugs loaded into M1 macrophages may include at least one selected from the group consisting of cisplatin, doxorubicin, pemetrexed, gemcitabine, paclitaxel, vincristine, daunorubicin, vinblastine, actinomycin-D, docetaxel, etoposide, teniposide, bisantrene, homoharringtonine, Gleevec (STI-571), cisplatin, 5-fluorouracil, methotrexate, busulfan, chlorambucil, cyclophosphamide, melphalan, nitrogen mustard, nitrosourea, cetuximab, and sorafenib. It is preferable that the anticancer drug being used to achieve the purpose of the present disclosure is soluble in solvents such as distilled water and PBS. Molecularly, the anticancer drug may be preferably an anticancer drug having a functional group that may react with the particle surface of PLGA gold nano particles. Further, the M1 macrophages as a drug delivery system of the present disclosure may have 0.5 to 12.5 µg/ml of each of the photo-responsive material and the anticancer drug loaded therein. At a concentration below the above range, the effect of killing cancer cells is low, while at a concentration higher than the above range, there is a problem in that macrophages are killed before reaching the cancer tissue due to the toxicity of the loaded anticancer drug. The concentration range may vary depending on the cytotoxicity of the anticancer drug loaded therein. On the other hand, in the anticancer treatment, it is common to administer an anticancer drug of a maximum tolerance dose at intervals of 3 to 4 weeks due to the rapid proliferation of cancer cells. However, the anticancer drugs have the disadvantage of having side effects by acting on bone marrow cells having a fast proliferation rate in addition to cancer cells. The present disclosure relates to M1 macrophages having material (photo-responsive material and/or anticancer drug) used for anticancer treatment loaded thereon. This scheme is to minimize the effect of the material loaded on the M1 macrophages on normal tissues and cells using the rapid movement of M1 macrophages into the tumor (cancer) and strong penetration ability, and is to allow the loaded material to act only on the tumor (cancer) cells and the surrounding microenvironment.

On the other hand, metronomic chemotherapy is a modified treatment form of anticancer treatment, and has the advantage of having few or no side effects by constantly administering an anticancer drug at a lower dose than a general administration dose. The metronomic chemotherapy does not directly kill cancer cells, but may inhibit the growth, proliferation, and/or metastasis of cancer cells, such as interfering with angiogenesis by acting on the tumor microenvironment. The M1 macrophages of the present disclosure is provided as a drug delivery system and may target only the cancer cells so that the loaded anticancer drug thereon may act only on the cancer cells (tumor). Therefore, when the drug delivery system of the present disclosure is used for the metronomic chemotherapy, it is possible to efficiently control the composition of the tumor microenvironment using a smaller dose of anticancer drug.

In one embodiment of the present disclosure, the present inventors incubated M1 macrophages containing PLGA-DOX therein with cancer cells and observed the macrophages for 0 to 72 hours in order to identify the release pattern of the anticancer drug loaded onto M1 macrophages therefrom. As a result, it was found that the M1 macrophages released the drug in a sustained-release manner for 24 hours to prevent cancer cell proliferation and induce apoptosis (see Example 5 to Example 3).

Since the drug delivery system of the present disclosure ultimately serves to deliver the anticancer drug loaded into the M1 macrophages to cancer (tumor) tissue, the drug delivery system may be provided as a pharmaceutical composition for enhancing the effect of an anticancer drug and a pharmaceutical composition for the prevention or treatment of cancer (tumor).

"Treatment" in the present disclosure means any action in which the symptoms of the tumor (cancer) are reduced or changed to a beneficial effect via administration of the composition and/or drug delivery system of the present disclosure. "Prevention" means any action that inhibits or delays the occurrence, metastasis, or recurrence of a tumor (cancer) via administration of the composition and/or drug delivery system of the present disclosure. "Effect enhancement" means that when a drug or a photo-responsive material loaded onto the M1 macrophages is used in a loaded manner into the M1 macrophages, the drug or photo-responsive material has a superior effect than when a drug or a photo-responsive material loaded onto the M1 macrophages is used alone. In the present disclosure, "pharmaceutical composition" means a product produced for the purpose of preventing or treating a disease, and may be formulated in various forms according to a conventional method. For example, it may be formulated in the formulation for oral administration such as powders, granules, tablets, capsules, suspensions, emulsions, and syrups, and may be formulated in the form of external preparations, suppositories, and sterile injection solutions.

Further, according to each formulation, pharmaceutically acceptable carriers, such as buffers, preservatives, analgesics, solubilizers, isotonic agents, stabilizers, bases, excipients, lubricants, etc. which are well known to the art may be added to the composition.

On the other hand, the pharmaceutical composition according to the present disclosure may be administered in a pharmaceutically effective amount. The term "pharmaceutically effective amount" in the present disclosure means an amount at a level that is sufficient to treat a disease with a reasonable benefit/risk ratio applicable to medical treatment and which will not cause side effects. The effective dose level may be determined according to factors including the patient's health status, severity, drug activity, sensitivity to drug, administration method, administration time, administration route and excretion rate, duration of treatment, combination or concurrent drugs, and other well-known factors in the medical fields.

Therefore, administering the pharmaceutical composition according to the present disclosure to a subject may prevent or treat cancer (tumor), and enhance the effect of anticancer treatment.

In the present disclosure, the "subject" may be a mammal, such as a rat, livestock, mouse, or human, preferably a human.

The pharmaceutical composition according to the present disclosure may be formulated in various forms for administration to a subject, and a representative formulation for parenteral administration is an injection formulation, preferably an isotonic aqueous solution or suspension. Formulations for injection may be produced according to techniques known in the art using suitable dispersing or wetting agents and suspending agents. For example, each component may be dissolved in saline or buffer to be formulated for injection. Further, the formulation for oral administration includes, for example, ingestible tablets, buccal tablets, troches, capsules, elixirs, suspensions, syrups, and wafers. These formulations contain, in addition to the active ingredient, diluents (e.g., lactose, dextrose, sucrose, mannitol, sorbitol, cellulose and/or glycine) and glidants (e.g., silica, talc, stearic acid and its magnesium or calcium salts and/or or polyethylene glycol). The tablet may contain a binder such as magnesium aluminum silicate, starch paste, gelatin, tragacanth, methylcellulose, sodium carboxymethylcellulose and/or polyvinylpyrrolidine. In some cases, a disintegrant such as starch, agar, alginic acid or a sodium salt thereof, an absorbent, a coloring agent, a flavoring agent and/or a sweetening agent may be additionally contained therein. The formulation may be produced by conventional mixing, granulating or coating methods.

Further, the pharmaceutical composition according to the present disclosure may further include adjuvants such as preservatives, wetting agents, emulsification accelerators, salts or buffers for regulating osmotic pressure, and other therapeutically useful materials, and may be formulated according to conventional methods.

The pharmaceutical composition according to the present disclosure may be administered via several routes including oral, transdermal, subcutaneous, intravenous or intramuscular. The dosage of the active ingredient may be appropriately selected according to several factors such as the route of administration, age, sex, weight of patient and a severity thereof. Further, the composition according to the present disclosure may be administered in parallel with a known compound that may enhance the intended effect.

The route of administration of the pharmaceutical composition according to the present disclosure may include administration thereof to the subject orally or parenterally, such as intravenously, subcutaneously, intranasally or intraperitoneally. Oral administration includes sublingual application. Parenteral administration includes injection methods such as subcutaneous injection, intramuscular injection, and intravenous injection and drip method.

In the pharmaceutical composition according to the present disclosure, a total effective amount of the M1 macrophages having the anticancer drug or the photo-responsive material loaded thereon according to the present disclosure may be administered to the patient at a single dose. Multiple doses may be administered to the subject based on a fractionated treatment protocol in which the administration is prolonged.

The pharmaceutical composition according to the present disclosure may have the content of the active ingredient varying according to the level of the disease. In general, when administered once for adults, an effective dose of 100 μg to 3,000 mg may be repeatedly administered several times a day, but the administration period is preferably not more than 24 hours. However, the concentration of M1 macrophages having the anticancer drug and/or photo-responsive material loaded thereon depends not only on the route of administration and the number of treatments, but also on various factors such as the patient's age, weight, health status, sex, disease severity, diet and excretion rate. Taking these factors into consideration, the effective dosage for the patient may be determined. Therefore, considering these points, those of ordinary skill in the art may determine an appropriate effective dosage according to a specific use of the M1 macrophages having the anticancer drug or photo-responsive material loaded thereon as a treatment agent or a prevention agent of the cancer (tumor). On the other hand, when the M1 macrophages of the present disclosure is administered for the prevention or treatment of cancer, the M1 macrophages may be locally administered to a location around the cancer tissue, may minimize the effect on normal cells that occur during intravenous injection, and may be administered at a higher dose than the dose at which the conventional anticancer drug is administered in consideration of stability.

Further, the pharmaceutical composition according to the present disclosure may additionally include known anticancer drugs (including angiogenesis inhibitors) or photo-responsive materials in addition to the M1 macrophages having the loaded material thereon as an active ingredient and may be used in combination with other treatments known for the treatment of these diseases.

EXAMPLES

The present disclosure may have various modifications and may have various examples. Thus, hereinafter, specific examples are illustrated in the drawings and described in detail in the detailed description. However, this is not intended to limit the present disclosure to specific examples. The disclosure should be understood as including all variations, equivalents to, and substitutes included in the spirit and scope of the present disclosure. In describing the present disclosure, when it is determined that a detailed description of a related known step or element may obscure the gist of the present disclosure, a detailed description thereof will be omitted.

EXAMPLE

Example 1. Preparation of M1 Macrophage

For the study of effective photo-thermal treatment method, we tried to identify the effects based on different types of macrophages according to varying differentiation methods. M1 macrophages is an anti-inflammatory macrophage. In order to differentiate macrophages into M1 macrophage, macrophages were first treated with PMA (Phorbol-12 Myristate 13-Acetate) to induce the M0 state, and then the M0 state was rested for 6 days. Then, the M0 macrophages were treated with IFN-γ (Interferon gamma) at a concentration of 200 μg/ml for 24 hours. To identify differentiation thereof into M1 macrophage, iNOS (Inducible nitric oxide synthase) mRNA expression levels were identified.

Further, for differentiation of macrophages into M2 macrophages related to tumor growth and metastasis, macrophages were first treated with PMA to induce the M0 state, and the M0 state was rested for 6 days. Subsequently, the M0 macrophages were treated with IL-4 at a concentration of 200 μg/ml for 24 hours. To identify differentiation thereof into M2 macrophage, the mRNA expression levels of Arginase1 and CD80 were identified.

As a result, as shown in FIG. 1, we prepared the differentiated M1 macrophages and M2 macrophages as prepared using the above method.

Example 2. Preparation of Nanoparticle-Loaded Macrophages

After preparing the PLGA-core gold nanoshells and putting the same in a macrophages culture medium, loading thereof into the macrophages were induced at room temperature for 2 hours using an orbital shaker. Then, after culturing for 2 hours in an incubator at 37° C., floating cells were removed, and only adherent cells were separated therefrom and were used.

Example 3. Identification of Migration of Macrophages to Tumor Cells According to Macrophages Types A tumor-bearing mouse model was prepared by injecting tumor cells into immunodeficient nude mice, and macrophages transfected with each luciferase gene were injected into 4 areas around the tumor. In order to eliminate the result that appear as mobility due to the division of macrophages in in vivo conditions, test groups were divided into a macrophages administered group; a macrophages and mitomycin C administered group; a M1 macrophages administered group; and a M1 macrophages and mitomycin C administered group. In this connection, the mitomycin C is a reagent that inhibits cell division and was used to exclude migration due to cell division in the observation of macrophages migration. The mobility of each macrophages injected into the mouse was measured through luminescence image tracking using the in vivo imaging technique. Imaging was performed before and after macrophages administration every 12 hours.

Figure 2:
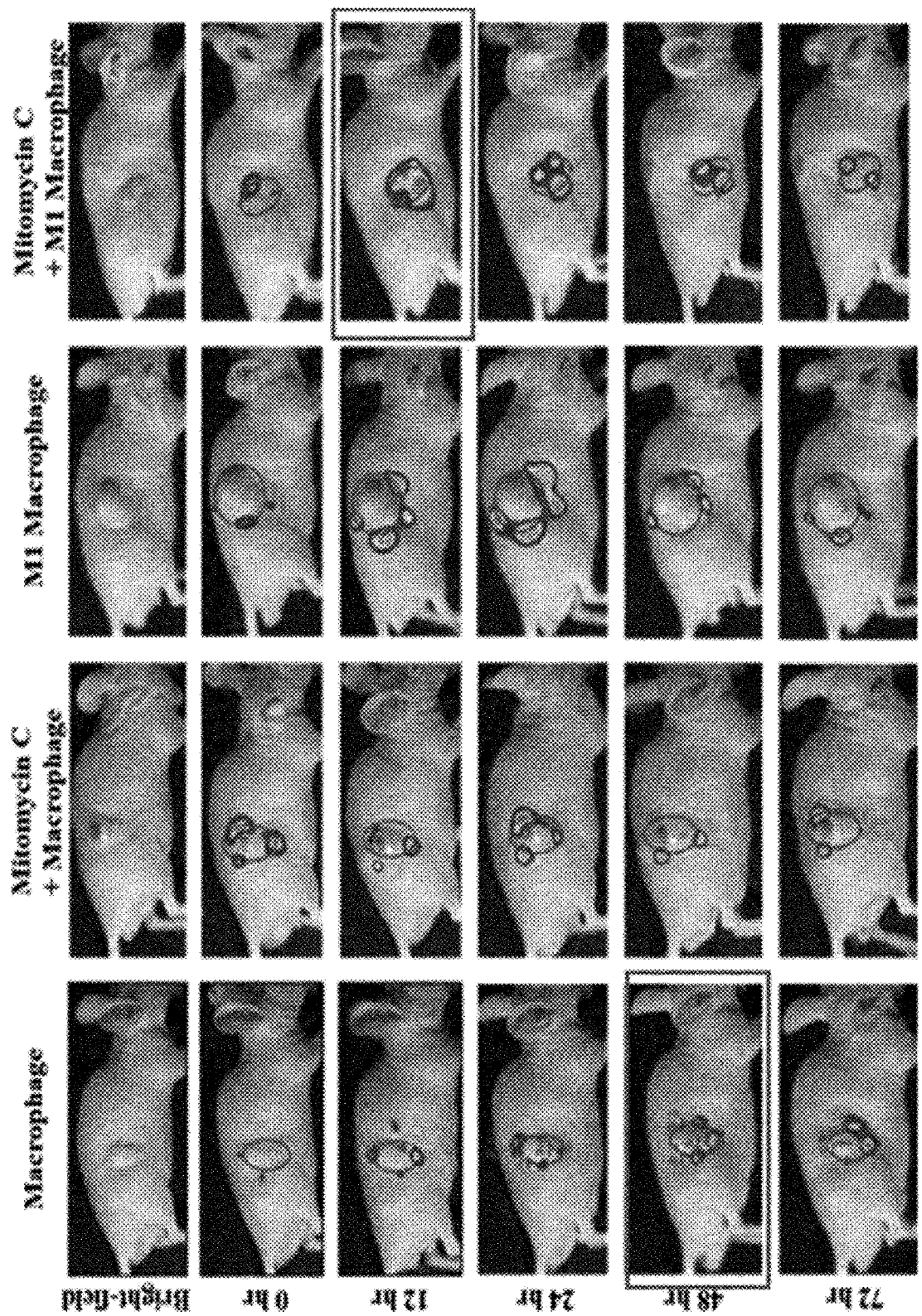
FIG. 2 is an in vivo imaging diagram that identifies the movement of macrophages over time.

As a result, as shown in FIG. 2, it was identified that when undifferentiated macrophages were injected, it took about 48 hours for the same to move into the tumor (red circle shown in each image in FIG. 2), whereas when M1 macrophages and mitomycin C were injected, it took about 12 hours for the same to migrate to the center of the tumor. From the above results, it may be identified that macrophages differentiated into M1 type have better mobility to the tumor, and faster drug (nanoparticles, etc.) access to the tumor is possible via the use of M1 macrophage, and the drug may reach the center of the tumor.

Example 4. Identification of Effect of Photo-Thermal Treatment Using M1 Macrophage 4-1. Identification of Effect of Photo-Thermal Treatment In Vitro
In order to identify the photo-thermal treatment effect according to the type of macrophage, M0, M1, or M2 macrophages loaded with nanoparticles (PLGA) were co-cultured with cancer cells at different concentrations. Then, the laser was irradiated thereto and thus the photo-thermal treatment effect was identified according to the cell density (low density: 70% confluency, high density: 90% confluency).

Figure 3:
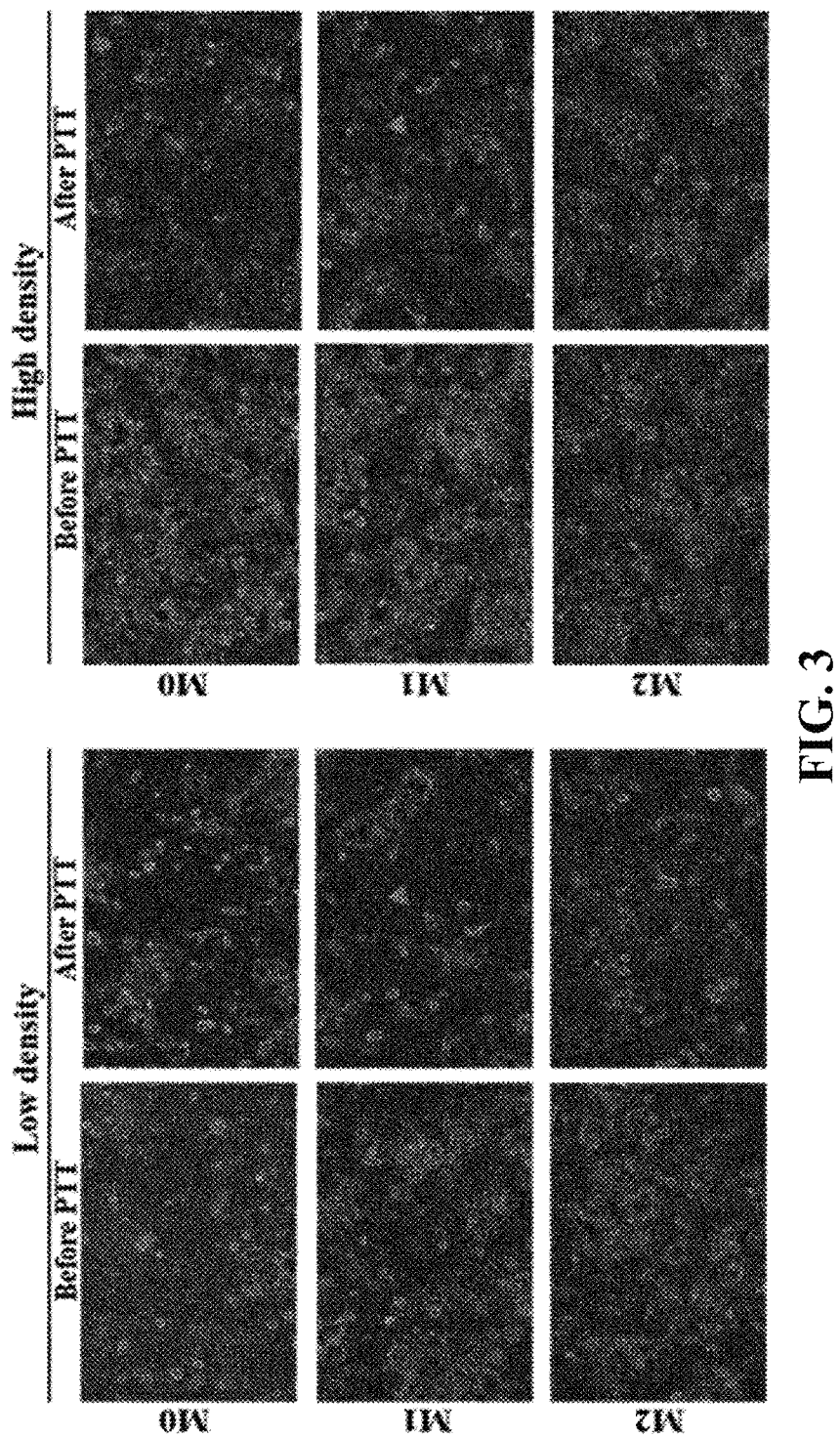
FIG. 3 is a diagram identifying comparisons of the effects of photo-thermal treatments based on the types of macrophages in vitro.

As a result, as shown in FIG. 3, it may be identified that a lot of cancer cells are killed when M1 macrophages and cancer cells were co-cultured regardless of macrophages density. Thus, when the M1 macrophages loaded with nanoparticles are used for the photo-thermal treatment, the treatment effect is more excellent.
4-2. Identification of Effect of Photo-Thermal Treatment In Vivo
Subsequently, in order to identify the function of enhancing the photo-thermal treatment effect using the M1 macrophages in vivo, we injected undifferentiated macrophages or M1 macrophages together with mitomycin C into the tumor-bearing mouse. When 1 day or 4 days elapsed since the photo-thermal treatment, the size of the tumor was measured.

Figure 4:
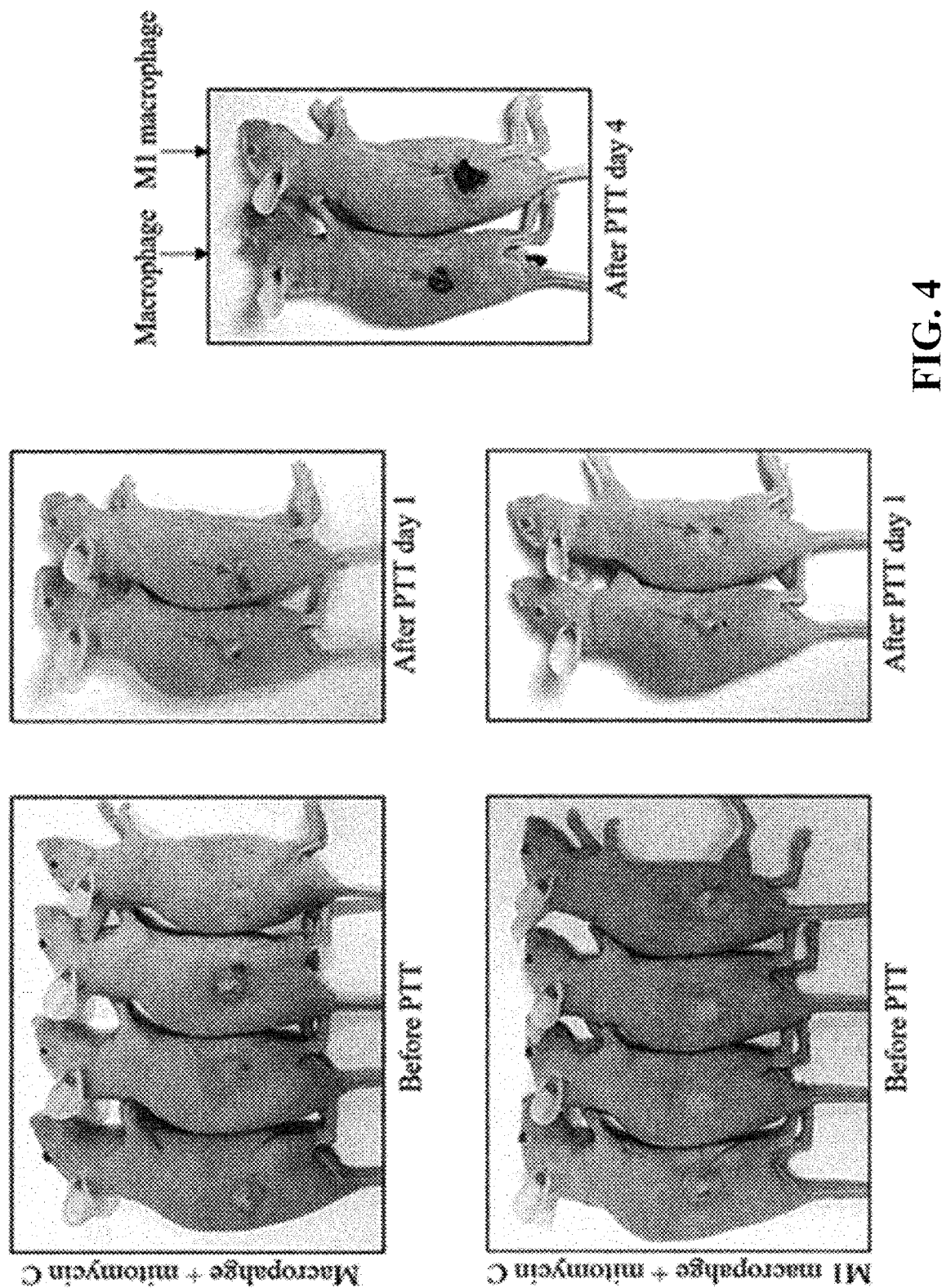
FIG. 4 is a diagram identifying comparisons of the effects of photo-thermal treatments based on the types of macrophages in vivo.

As a result, as shown in FIG. 4, it was identified that when M1 macrophages were injected, the size of the tumor decreased sharply from 1 day after the photo-thermal treatment, compared to the case where undifferentiated macrophages were injected. Further, it was identified that when 4 days elapsed after the photo-thermal treatment, the tumor was removed and only skin tissue remained.

Example 5. Identification of Delivery Effect of Photo-Responsive Material and Anticancer Drug Using M1 Macrophage 5-1. Loading of Photo-Responsive Material and Anticancer Drug into M1 Macrophages
After preparing a mixture of anticancer drug and photo-responsive material (PLGA-core gold nanoshells) to have a final concentration of 1 mg/ml, we added the mixture to the macrophages culture medium according to the anticancer drug test condition, that is, 0.02 to 62.5 μg/ml, and then the loading of the drug and the material into the macrophages was induced for 2 hours at room temperature using an orbital shaker. Then, after removing the supernatant through centrifugation, only the cells as obtained were used.
5-2. Identification of Anticancer Drug Delivery Effect to Cancer Cells Using M1 Macrophages
In order to identify whether M1 macrophages may be delivered to the inside of the tumor without being killed even after incorporation of the anticancer drug therein, the viability of M1 macrophages loaded with different concentrations of anticancer drug (doxorubicin: DOX) was identified through MTT assay. The time it takes for M1 macrophages to migrate to cancer cells was usually considered to be 12 hours. Thus, when 6, 12, and 24 hours elapsed after the loading of PLGA+Doxorubicin into the M1 macrophages at various concentrations (0, 0.02, 0.1, 0.5, 2.5, 12.5, or 62.5 μg/ml), cell viability was observed.

Based on a result of comparing the resistances of undifferentiated macrophages (RAW cell) and differentiated M1 macrophage against cytotoxicity by the anticancer drug incorporated therein at the same concentration and for the same time duration with each other, it was identified that a cell death rate of the M1 macrophage was lower. Thus, it was found that M1 macrophages were less affected by the toxicity of the incorporated anticancer drug therein than undifferentiated macrophage were.

Figure 5:
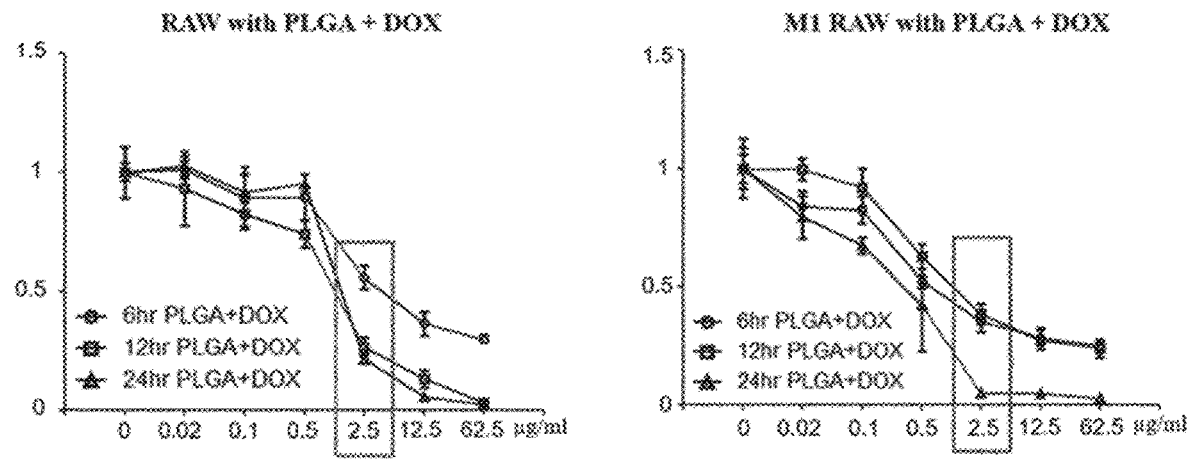
FIG. 5 is a diagram showing the cell viability of macrophages containing PLGA-DOX at a concentration of 0 to 62.5 μg/ml.
Figure 6:
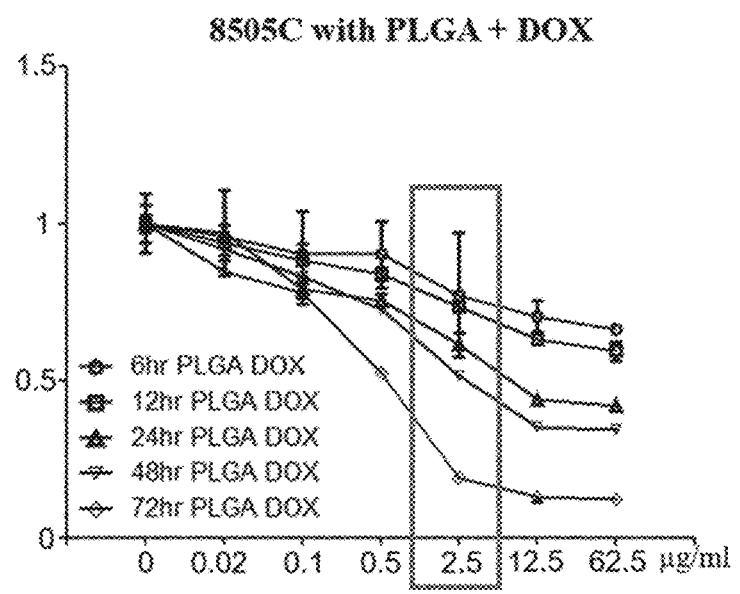
FIG. 6 is a diagram identifying the cancer cell death-inducing effect of M1 macrophages containing PLGA-DOX at a concentration of 2.5 μg/ml.

Because the death of cancer cells is gradually observed 12 hours after administration of M1 macrophages, it is desirable that the anticancer drug incorporated into M1 macrophages exhibits viability of 50% or higher for 12 hours and, at the same time, has the lowest concentration among the concentrations in which cancer cell death occurs. It was identified that M1 macrophages having the drug loaded thereon at a concentration of 2.5 μg/ml exhibited 50% viability 12 hours after the loading (FIG. 5), and thus most of cancer cells were killed 72 hours after the administration (FIG. 6). From the above results, it may be identified that the optimal concentration of the anticancer drug to be incorporated into M1 macrophages is 2.5 μg/ml. Thus, M1 macrophages containing about 2.5 μg/ml of the anticancer drug and the photo-responsive material therein are delivered to cancer tissue, thereby effectively inducing apoptosis of cancer cells.
5-3. Identification of Drug Release Form of M1 Macrophage
Then, PLGA and DOX were loaded into undifferentiated macrophages and M1 macrophage. Two in-vitro modeling experiments were performed to re-verify the effectiveness of M1 macrophages as a drug delivery system and to identify the drug release form from the M1 macrophages.

Figure 7:
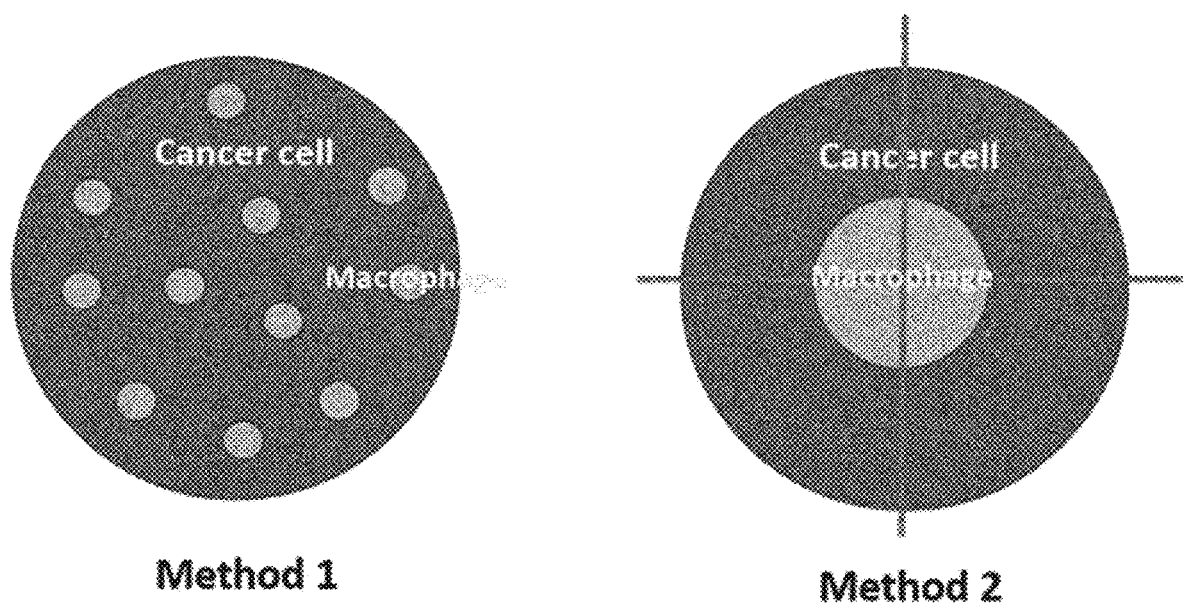
FIG. 7 is an experimental schematic diagram for identifying the drug release pattern of M1 macrophages containing PLGA-DOX.

Specifically, four groups, that is, macrophage, macrophages+PLGA-DOX, MI macrophage, and M1 macrophages+PLGA-DOX were prepared. The macrophages of each group were simultaneously cultured with cancer cells. Then, whether the cancer cells were killed, and the death percentage were identified via observation for up to 0 to 72 hours. (FIG. 7, Method 1). Further, in order to separate cancer cells and macrophages from each other, a cylindrical peni cylinder was placed on a center of a plate. Thus, macrophages were placed inside the cylinder, and cancer cells were cultured outside the cylinder. Then, we identified the mobility of macrophages into cancer cells and an amount at which the anticancer drug released therefrom was maintained (FIG. 7, Method 2).

Figure 8:
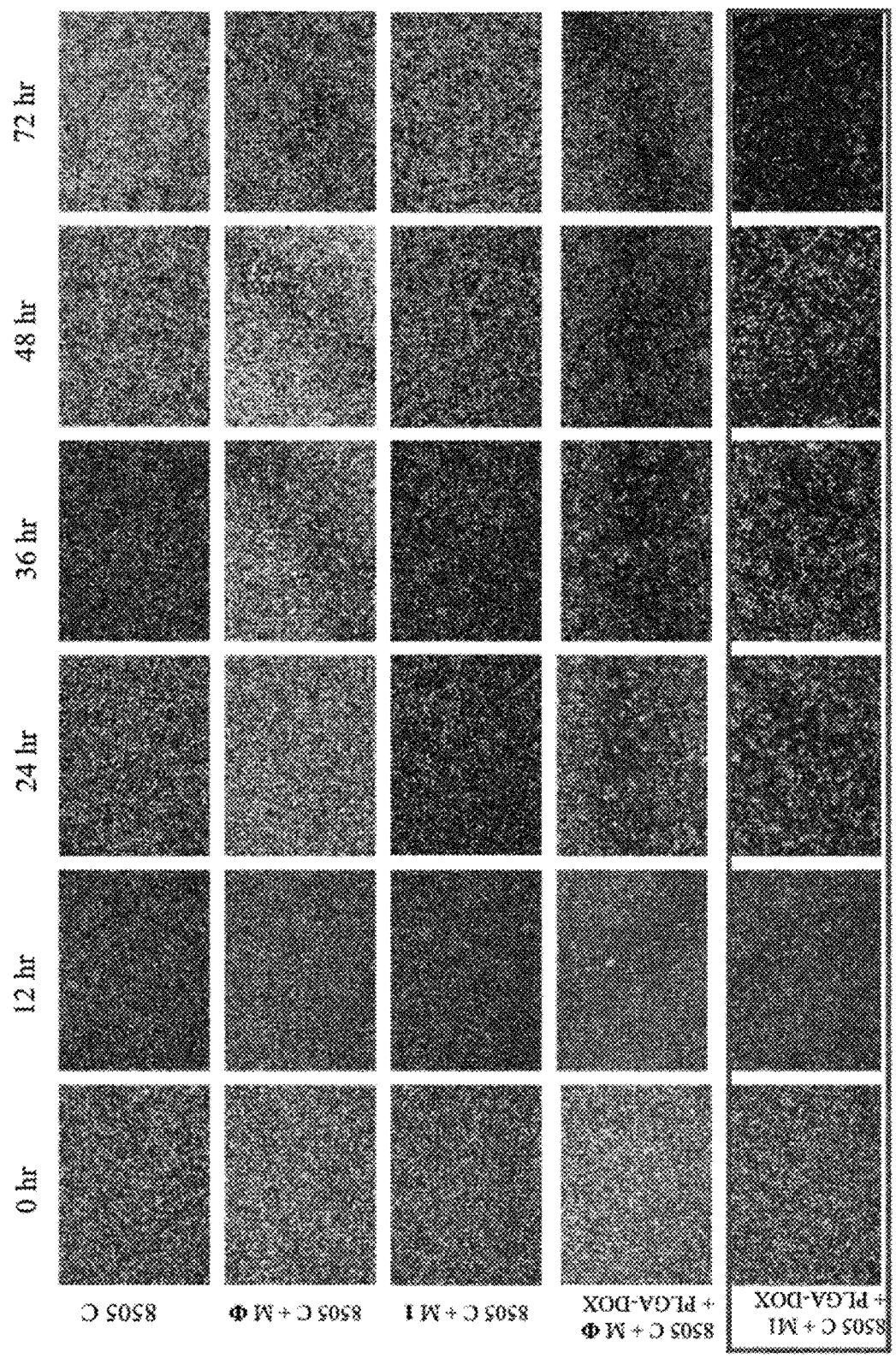
FIG. 8 is the experimental result of Method 1.

Based on a result of the experiment in Method 1, it was identified that macrophages exhibited the cancer cell killing effect for a certain period of time only when the macrophages were co-cultured with the cancer cells. However, the cancer cell killing effect was excellent when using the M1 macrophages rather than when using the undifferentiated macrophage. It was identified that the cancer cell killing effect was the most excellent when using the M1 macrophages containing PLGA and DOX therein (FIG. 8). From the above results, it may be identified that the loaded anticancer drug is released from the macrophage.

Figure 9:
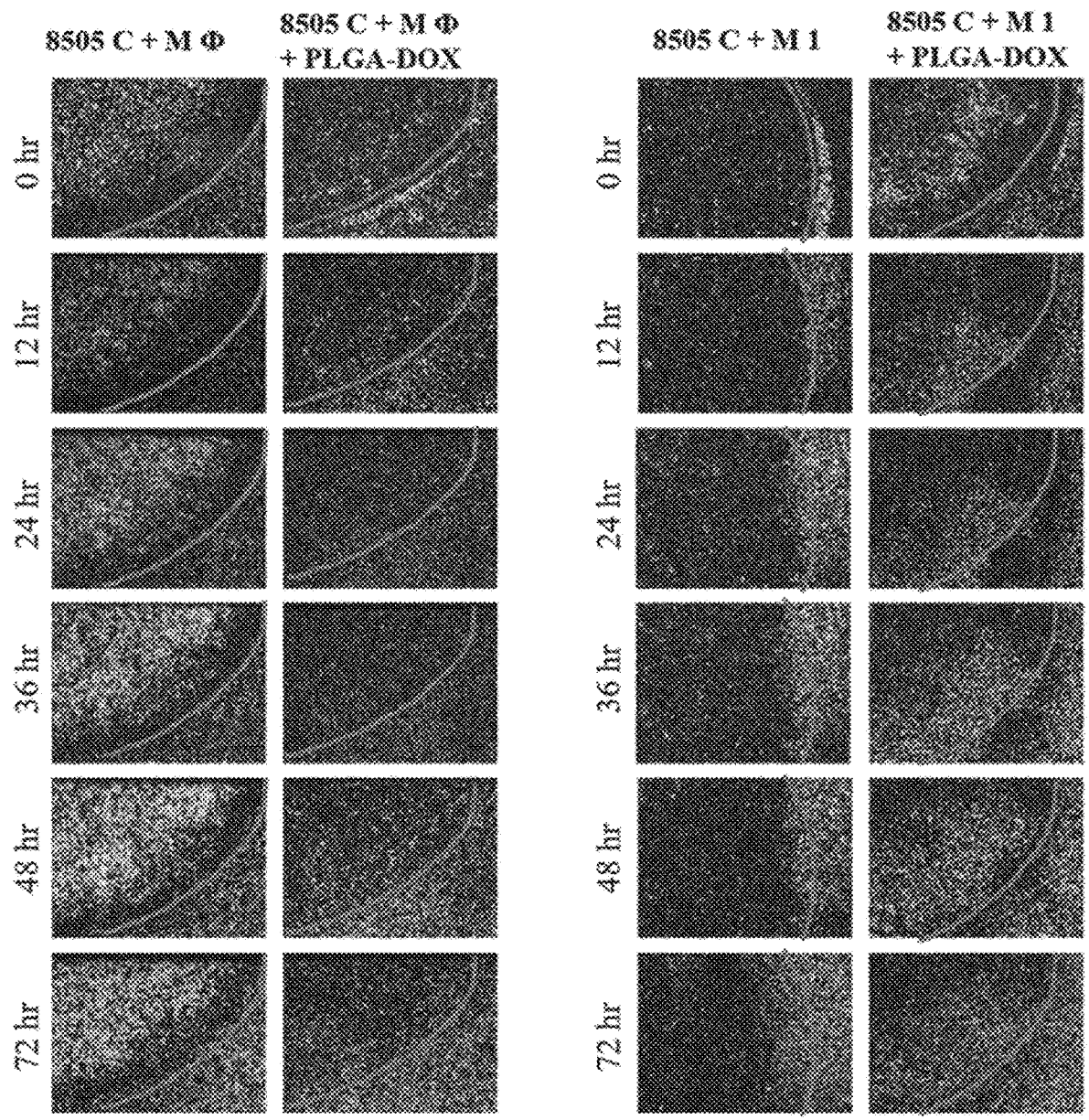
FIG. 9 is the experimental result of Method 2.

The experimental results of Method 2 are shown in FIG. 9, and the left side around the red line in FIG. 9 is directed to macrophages and the right side around the red line is directed to cancer cell. In the undifferentiated macrophages administered group (macrophages and macrophage+PLGA-DOX), macrophages migration and cancer cell death were not observed at all time points. On the other hand, in the plate cultured with the M1 macrophage, cancer cells did not proliferate for up to 12 hours. However, after 12 hours, proliferation due to the division of cancer cells was identified, which is thought to be due to the decrease in the effect of the cytokine secreted from the M1 macrophage. On the other hand, when the M1 macrophages group loaded with PLGA and DOX were injected, the effect of macrophages infiltrating into cancer cells and the killing effect of the cancer cells were observed for 0 to 24 hours. However, after 24 hours, cancer cell proliferation was also observed in the M1 Macrophage+PLGA-DOX administered group. This means that the M1 macrophages containing 2.5 μg/ml of PLGA-DOX therein release the anticancer drug therefrom for 24 hours and then died and thus did not exhibit the effect of killing cancer cells.

The present disclosure may be implemented in various modified manners within the scope not departing from the technical idea of the present disclosure. Accordingly, the embodiments disclosed in the present disclosure are not intended to limit the technical idea of the present disclosure, but to describe the present disclosure. The scope of the technical idea of the present disclosure is not limited by the embodiments. Therefore, it should be understood that the embodiments as described above are illustrative and non-limiting in all respects. The scope of protection of the present disclosure should be interpreted by the claims, and all technical ideas within the scope of the present disclosure should be interpreted as being included in the scope of the present disclosure.

INDUSTRIAL APPLICABILITY

The present disclosure is expected to be usefully used to enhance the effect of photo-thermal treatment or to reduce the side effects of anticancer drugs and enhance their efficacy.

The invention claimed is:
1. A method for producing cell targeting anticancer M1 macrophages, the method comprising:
 (1) treating isolated undifferentiated macrophages with PMA (Phorbol-12 Myristate 13-Acetate) to induce an M0 macrophages state;
 (2) treating the M0 macrophages with IFN-γ (Interferon gamma) at a concentration of 100 to 400 μg,ml for 24 to 48 hours to induce differentiation into the M1 macrophages;
 (3) preparing a mixture by mixing an anticancer drug with a photo-responsive material to a final concentration of 1 μg/ml for the photo-responsive material and 2.5 μg/ml for the anticancer drug:
 (4) adding the mixture to the culture medium of the M1 macrophages and using an orbital shaker at room temperature for 2 hours to induce incorporation of the photo-responsive material and anticancer drug into the M1 macrophages; and
 (5) Centrifuging the culture medium containing the mixture and M1 macrophages to remove the supernatant and obtaining M1 macrophages containing the photo-responsive material and anticancer drug;
 wherein the photo-responsive material is PLGA-core gold nanoshells, and the anticancer drug is doxorubicin.
2. The method of claim 1, wherein the method further comprises resting the M0 macrophages for 3 to 9 days after the (1).

* * * * *